US008703200B2

(12) United States Patent
McGinnis et al.

(10) Patent No.: US 8,703,200 B2
(45) Date of Patent: Apr. 22, 2014

(54) INHIBITION OF NEOVASCULARIZATION BY CERIUM OXIDE NANOPARTICLES

(75) Inventors: James F. McGinnis, Edmond, OK (US);
Xiaohong Zhou, Arlington, MA (US);
Lily L. Wong, Oklahoma City, OK (US);
Sudipta Seal, Orlando, FL (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 189 days.

(21) Appl. No.: 12/429,650

(22) Filed: Apr. 24, 2009

(65) Prior Publication Data

US 2009/0269410 A1 Oct. 29, 2009
US 2012/0093931 A9 Apr. 19, 2012

Related U.S. Application Data

(63) Continuation-in-part of application No. 11/412,665, filed on Apr. 27, 2006, now Pat. No. 7,727,559.

(60) Provisional application No. 60/716,630, filed on Sep. 13, 2005, provisional application No. 60/676,043, filed on Apr. 29, 2005, provisional application No. 61/125,602, filed on Apr. 25, 2008.

(51) Int. Cl.
*A61K 9/14* (2006.01)
*A01N 59/16* (2006.01)
*A61K 33/24* (2006.01)

(52) U.S. Cl.
USPC ............................................ 424/489; 424/617

(58) Field of Classification Search
USPC ................................................ 424/489, 617
See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussourira | |
| 5,961,993 A | 10/1999 | Boussourira | |
| 6,042,714 A | 3/2000 | Lin et al. | |
| 6,103,247 A | 8/2000 | Boussourira | |
| 6,139,985 A | 10/2000 | Borglum et al. | |
| 6,316,012 B1 | 11/2001 | N'Guyen | |
| 6,327,074 B1 | 12/2001 | Bass et al. | |
| 6,368,577 B1 | 4/2002 | Kropf et al. | |
| 6,406,685 B1 | 6/2002 | Philippe | |
| 6,468,551 B1 | 10/2002 | Diec | |
| 6,497,863 B1 | 12/2002 | Wachter | |
| 6,497,875 B1 | 12/2002 | Sorrell et al. | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 * | 5/2005 | Shashoua | 514/5.5 |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugama | |
| 7,534,453 B1 | 5/2009 | Rzigalinski et al. | |
| 7,563,459 B2 | 7/2009 | Phillips et al. | |
| 7,642,250 B2 | 1/2010 | Williams | |
| 7,687,505 B2 | 3/2010 | Sugaya | |
| 7,725,802 B2 | 5/2010 | Katusic et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfield et al. | |
| 7,924,617 B2 | 4/2011 | Yadav | |
| 8,080,420 B2 | 12/2011 | Sugaya | |
| 8,097,270 B2 | 1/2012 | Ketelson et al. | |
| 8,172,901 B2 | 5/2012 | Altman et al. | |

(Continued)

FOREIGN PATENT DOCUMENTS

| | | | |
|---|---|---|---|
| WO | WO 99/15891 A2 | | 4/1999 |
| WO | WO 03/059263 | * | 7/2003 |
| WO | WO 03/059263 A2 | | 7/2003 |
| WO | 2006118954 | | 11/2006 |
| WO | WO 2006/118954 A2 | | 11/2006 |
| WO | 2007002662 | | 1/2007 |
| WO | WO 2007/002662 A2 | | 1/2007 |
| WO | WO 2008/064357 A2 | | 5/2008 |
| WO | PCT/US2009/041675 | | 6/2009 |
| WO | WO 2009/132277 A2 | | 10/2009 |
| WO | PCT/US2011/044329 | | 12/2011 |

OTHER PUBLICATIONS

Birch, D. G.; Liang, F. Q. Age-related macular degenration: a target for nanotechnology derived medicines. International Journal of Nanomedicine, 2007, 2 (1), 65-77.*

(Continued)

*Primary Examiner* — Gina C Justice
*Assistant Examiner* — Genevieve S Alley
(74) *Attorney, Agent, or Firm* — Dunlap Codding, P.C.

(57) ABSTRACT

The present invention provides methods for reducing, reversing or inhibiting neovascularization in a tissue of a mammalian subject having a pathological condition involving neovascularization by administration in vivo of nanoceria particles (cerium oxide nanoparticles) to the subject. The method of the invention is useful, for example, for reducing, treating, reversing or inhibiting neovascularization in ocular tissue such as the retina, macula or cornea; in skin; in synovial tissue; in intestinal tissue; or in bone. In addition, the method of the invention is useful for reducing or inhibiting neovascularization in a neoplasm (tumors), which can be benign or malignant and, where malignant, can be a metastatic neoplasm. As such, the invention provides compositions, which contain nanoceria particles and are useful for reducing, treating, reversing or inhibiting angiogenesis in a mammalian subject.

10 Claims, 7 Drawing Sheets

(56) References Cited

U.S. PATENT DOCUMENTS

| | | | |
|---|---|---|---|
| 2003/0050709 | A1 | 3/2003 | Noth et al. |
| 2003/0187077 | A1 | 10/2003 | Chane-Ching |
| 2003/0228277 | A1* | 12/2003 | Gehlsen ............... 424/85.2 |
| 2004/0062753 | A1 | 4/2004 | Rezania et al. |
| 2005/0159820 | A1 | 7/2005 | Yoshikawa et al. |
| 2005/0164377 | A1 | 7/2005 | Miyabayashi et al. |
| 2005/0171192 | A1* | 8/2005 | Gehlsen ............... 514/458 |
| 2006/0110440 | A1 | 5/2006 | Sugaya |
| 2006/0280729 | A1 | 12/2006 | Mistry |
| 2007/0003621 | A1 | 1/2007 | Nangia et al. |
| 2007/0072825 | A1* | 3/2007 | Williams ............... 514/54 |
| 2009/0087493 | A1 | 4/2009 | Dai et al. |
| 2009/0098574 | A1 | 4/2009 | Brisson et al. |
| 2010/0151000 | A1 | 6/2010 | Thomas et al. |

OTHER PUBLICATIONS

Maulik, N. Reactive oxygen species drives myocardial angiogenesis? Antioxidants & Redox Signaling, 2006, 8 (11-12), 2161-2168.*

Ohia et al. Mutation Research, 2005, 579, 22-36.*

Birch et al. International Journal of Nanomedicine, 2007, 2 (1), 65-77.*

Liu et al. Braefe's Arch Clin Exp Ophthalmol, 2007, 245, 1441-1445.*

Silva, Nature Nanotechnology, 2006, 1, 92-94.*

Hahn et al. Arch. Ophthalmol. 2003, 121, 1099-1105.*

Haywood et al. Arthritis & Rhematism, 2003, 48 (8), 2173-2177.*

Hollyfield et al., "Oxidative damage-induced inflammation initiates age-related macular degeneration", *Nature Medicine*, vol. 14, pp. 194-198 (2008).

Imamura et al., "Drusen, choroidal neovascularization, and retinal pigment epithelium dysfunction on SOD1-deficient mice: A model of age-related macular degeneration" *PNAS*, vol. 103, No. 30, pp. 11282-11287 (Jul. 25, 2006).

U.S. Appl. No. 12/772,523, McGinnis et al., Office Action mailed Sep. 15, 2011.

Chen, et al; "Rare Earth Nanoparticles Prevent Retinal Degeneration Induced by Intracellular Peroxides"; Nature Nanotechnology, 1(2) 142-148 (2006).

Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinskill.html, p. 1 only.

Buettner, et al. "Ascorbate (Vitamin C), its Antioxidant Chemistry" [PDF Powerpoint] Virtual Free Radical School for Oxygen Society (2002).

Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm?new_page_id=126&abstract_id=14513&p_num=669.13&is_tech=0> [retrieved on Aug. 5, 2008] *abstract*, p. 1 only.

Devasenpathi, et al. Mat. Let. 57: 882-886; 2002.

Dong, et al. "Activation of glassy carbon electrodes by dispersed metal oxide particles." J. Electrochem Soc., 1984, 813-819, p. 1 only.

Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272, p. 1 only.

Heckert, et al. "The role of cerium redox state in the SOD mimetic activity of nanoceria," Biomaterials, 29, 2008, pp. 2705-2709, US, p. 1 only.

Hooper, Claire, Y., et al. "New Treatment in age-related macular degeneration" Clinical & Experimental Opthalmology, Oct. 2003, pp. 376-391, XP002491214 ISSN: 1442-6404 *pp. 378-382*, p. 1 only.

Jin, et al. "Nanopartical-mediated drug delivery and gene therapy," Biotechnol. Prog, 2007, vol. 23, pp. 32-41, p. 1 only.

Karakoti, et al. "Direct Synthesis of Nanoceria in Aqueous Polyhydroxyl Solutions." J. Phys. Chem. C, vol. 111, No. 46, 2007, pp. 17232-17240, US, p. 1 only.

Margrain, T.H., et al. "Do blue light filters confer protection against age-related macular degeneration?" Progress in Retinal and Eye Research, vol. 23 (2004) pp. 523-531, p. 1 only.

Maschio, et al. J. Mat. Sci. 27: 5591-5596; 1992, p. 1 only.

Moongkarndi, et al. "Antiproliferation, antioxidation and induction of apoptosis by *Garcinia mangostana* (mangosteen) on SKBR3 human breast cancer cell line," J. of Ethno-Pharmacology, vol. 90, (2004) pp. 161-166, p. 1 only.

Nafee. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch-Technischen Fakul't III Chemie, Pharmazie, Bio-und Werstoffwissenschaften der Universit des Saarlandes, 2008, p. 1 only.

Nazem, et al. "Nanotechnology for Alzheimer's disease detection and treatment." Insciences J. 2011, vol. 1(4), pp. 169-193; published Oct. 4, 2011, p. 1 only.

Niu, J., et al. "Cardiovascular effects of cerium oxide nanoparticles in a transgenic murine model of cardiomyopathy," Cardiovas. Res. Nov. 30, 2006, vol. 73, No. 3, pp. 549-559.

Ohgushi, et al. J. Biomed. Mat. Res. 48: 913-927; 1999, p. 1 only.

Olivier, et al. "Synthesis of pegylated immunonanoparticles." Pharmaceutical Research, Aug. 2002, vol. 19, No. 8, pp. 1137-1143, p. 1 only.

Otsuka, et al. "PEGylated nanoparticles for biological and pharmaceutical applications," Advanced Drug Delivery Reviews, 2003, vol. 55, pp. 403-419, p. 1 only.

Patil, et al. "Synthesis of nanocrystalline ceria particles for high temperature oxidation resistant coating," Journal of Nanoparticle Research, 2002, vol. 4: ppl. 433-438, p. 1 only.

Patil, et al. "Surface-derived nanoceria with human carbonic anhydrase II inhibitors and flourphores: a potential drug delivery device." J. Phys. Chem. C., 2007, vol. 111, No. 24, pp. 8437-8442, p. 1 only.

Perez, J. M., et al. "Synthesis of Biocompatible Dextran-Coated Nanoceria with pH-Dependent Antioxidant Properties," Small, vol. 4 No. 5, 2008, pp. 552-556, published online Apr. 24, 2008, p. 1 only.

Pirmohamed, et al. "Nanoceria exhibit redox state-dependent catalase mimetic activity," Chem. Comm, 2010, 46, pp. 2736-2738, US, p. 1 only.

Qi, et al. "Redispersible Hybrid Nanopowders; Cerium Oxide Nanoparticle complexes with Phosphonated-PEG Oligomers," ACS Nano, 2008, vol. 2(5), pp. 879-888, p. 1 only.

Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287; Abstract; pp. 72 P7f*.

Ramsfjell, et al. Blood 99: 4093-41.2; 1999.

Rzigalinski, Beverly Ann, et al. "Cerium Oxide nanoparticles increase the lifespan of cultured brain cells and protect against free radical mechanical trauma" FASEB Journal, vol. 17 No. 4-5, Page Abstract No. 377.24 URL, XP008095016 & FASEB Meeting on Experimental Biology: Translating the Genome, San Diego, CA, USA, Apr. 11-15, 2003 ISSN: 0892-6638 *Abstract*, p. 1 only.

Schubert, et al. "Cerium and yttrium oxide nanoparticles are neuroprotective," Feb. 3, 2006, Biochemical and Biophysical Research Communications, 342, p. 86-91, p. 1 only.

Shui, Y.B., et al. "Morphological observation on cell death an dphagocytosis induced by ultraviolet irradiation in a cultured human lens epithelial cell line," Dec. 2000, vol. 71(6), abstract.

Sigma Alderich Handbook (2004), 400.

Sokolov, et al. "Real-time vital optical imaging of precancer using anti-epidermal growth factor receptor antibodies conjugated to gold nanoparticles." Cancer Res. 2003, vol. 63:1999, 2004, Title only.

Suh, et al "Multifunctional nanosystems at the interface of physical and life sciences." Physicaplus, Apr. 15, 2010, Issue No. 13 available online at <http://physicaplus.org.il/zope/home/en/1224031001/multi_nano_en>, p. 1 only.

(56) References Cited

OTHER PUBLICATIONS

Suzuki, et al "Preparation and characteristics of magnetitelabelled anitbody with the use of poly(ethylene glycol) derivatives," Biotechnol. Appl. Biochem., 1995, vol. 21, pp. 335-345, Abstract only.

Tarnuzzer, et al. "Vacancy Engineered Ceria Nanostructures for Protection from Radiation-Induced Cellular Damage," Nano Lett, vol. 4, No. 12, pp. 2573-2577, US *, p. 1 only; 2005.

Tsai, Ming-Shyong. "The Study of the synthesis of nano-grade cerium oxide powder," Materials Letters 58, 2270-2274 (2004), p. 1 only.

Tusnekawa, S., et al. "Lattice relaxation of monosize Ce02-x nanocrystalline particles" Applied Surface Science Elsevier Netherlands, vol. 152, No. 1-2, Nov. 1999, pp. 53-56, XP002491212 ISSN: 0169-4332 * p. 53, col. 1, paragraph 2—col. 2, paragraph 1, p. 1 only.

Xijuan, et al. "Size-dependent optical properties of nanocrystalline Ce02:Er obtained by combustion synthesis," Sep. 24, 2001, Phys. Chem. Chem Phys., vol. 3, pp. 5266-5269, p. 1 only.

Zhang, et al. Cerium oxide nanoparticles: size selective formation and structure analysis, Jan. 7, 2002, Applied Physics Letters, vol. 81, No. 1, p. 127-129.

Chen et al. Nature, 2006, 1, 142-150.*

Monte et al. Free Radic Biol Med., 1994, 17 (3), 259-266; abstract only.*

Guo. "Green and red upconversion luminescence in $CeO_2:Er^{3+}$ powders produced by 785 nm laser," Oct. 10, 2006, *Journal of Solid State Chemistry* 180, pp. 127-131.

* cited by examiner

C57　　　　　VLDLr + NaCl　　　　VLDLr + Nanoceria

INHIBITION OF NEOVASCULARIZATION BY CERIUM OXIDE NANOPARTICLES

CROSS-REFERENCE TO RELATED APPLICATIONS

The present application claims the benefit under 35 U.S.C. 119(e) of U.S. Provisional Application Ser. No. 61/125,602, filed Apr. 25, 2008, the entirety of which is hereby expressly incorporated herein by reference.

The present application is also a continuation-in-part of U.S. Ser. No. 11/412,665, filed Apr. 27, 2006, now U.S. Pat. No. 7,727,559 issued on Jun. 1, 2010, which claims the benefit under 35 U.S.C. §119(e) of U.S. Provisional Application Ser. No. 60/716,630, filed Sep. 13, 2005, and U.S. Provisional Application Ser. No. 60/676,043, filed Apr. 29, 2005.

STATEMENT REGARDING FEDERALLY SPONSORED RESEARCH OR DEVELOPMENT

Not applicable.

BACKGROUND OF THE INVENTION

Angiogenesis (also referred to herein as neovascularization) is the process whereby new blood vessels are formed. Angiogenesis occurs normally during embryogenesis and development, and occurs in fully developed organisms during wound healing and placental development. In addition, angiogenesis occurs in various pathological conditions, including in ocular diseases such as diabetic retinopathy and macular degeneration due to neovascularization, in conditions associated with tissue inflammation such as rheumatoid arthritis and inflammatory bowel disease, and in cancer, where blood vessel formation in the growing tumor provides oxygen and nutrients to the tumor cells, as well as providing a route via which tumor cells metastasize throughout the body. Since millions of people around the world are afflicted by these diseases, a considerable effort has been made to understand the mechanisms involved in angiogenesis in the hope that such an understanding will allow the development of methods for detecting and inhibiting such undesirable angiogenesis.

Angiogenesis occurs in response to stimulation by one or more known growth factors, and also may involve other as yet unidentified factors. Endothelial cells, which are the cells that line mature blood vessels, normally do not proliferate. However, in response to an appropriate stimulus, the endothelial cells become activated and begin to proliferate and migrate into unvascularized tissue forming new blood vessels. In some cases, precursor cells can be activated to differentiate into endothelial cells which form new blood vessels.

Blood vessels are surrounded by an extracellular matrix. In addition to stimulation by growth factors, neovascularization depends on interaction of the endothelial cells with the extracellular matrix, as well as with each other. The activation of endothelial cells by growth factors and the migration into and interaction with the extracellular matrix and with each other is dependent on cell surface receptors expressed by the endothelial cells. These cell surface receptors, which include growth factor receptors and integrins, interact specifically with particular molecules.

In pathological conditions such as age-related macular degeneration and diabetic retinopathy, decreasing availability of oxygen to the retina results in a hypoxic condition that stimulates the secretion of angiogenic growth factors such as vascular endothelial growth factors (VEGF), which induce abnormal migration and proliferation of endothelial cells into tissues of the eye. Such neovascularization in ocular tissues can induce corneal scarring, retinal detachment and fluid accumulation in the choroid, each of which can adversely affect vision and lead to blindness.

Angiogenesis also is associated with the progression and exacerbation of inflammatory diseases, including psoriasis, rheumatoid arthritis, osteoarthritis, and inflammatory bowel diseases such as ulcerative colitis and Crohn's disease. In inflammatory arthritic disease, for example, influx of lymphocytes into the region surrounding the joints stimulates angiogenesis in the synovial lining. The increased vasculature provides a means for greater influx of leukocytes, which facilitate the destruction of cartilage and bone in the joint. Neovascularization that occurs in inflammatory bowel disease results in similar effects in the bowel.

The growth of capillaries into atherosclerotic plaques in the coronary arteries represents another pathological condition associated with growth factor induced angiogenesis. Excessive blood flow into neovascularized plaques can result in rupture and hemorrhage of the blood-filled plaques, releasing blood clots that can result in coronary thrombosis.

The involvement of angiogenesis in such diverse diseases as cancer, ocular disease and inflammatory diseases has led to an effort to identify methods for specifically inhibiting angiogenesis as a means to treat these diseases. For cancer patients, such methods of treatment can provide a substantial advantage over currently used methods such as chemotherapy, which kill or impair not only the target tumor cells, but also normal cells in the patient, particularly proliferating normal cells such as blood cells, epithelial cells, and cells lining the intestinal lumen. Such non-specific killing by chemotherapeutic agents results in side effects that are, at best, unpleasant, and can often result in unacceptable patient morbidity, or mortality. In fact, the undesirable side effects associated with cancer therapies often limit the treatment a patient can receive.

For other pathological conditions associated with abnormal angiogenesis such as diabetic retinopathy, there are no effective treatments short of retinal transplants. However, even if retinal transplantation is performed, the new retina would be subject to the same conditions that resulted in the original retinopathy. Thus, there exists a need for novel methods of inhibiting and treating neovascularization in patients suffering from pathological conditions characterized by this condition. The present invention satisfies this need and provides related advantages as well in the treatment of other disease conditions identified herein.

The retina is the part of the eye that is sensitive to light. The macula lutea is the region of the retina that allows us to read and recognize faces. Diseases of the macula, such as age-related macular degeneration (AMD) and diabetic macular edema, account for a major proportion of legal blindness. To combat these diseases, a variety of accepted and experimental medications are employed via systemic routes or local, invasive surgical procedures.

Diabetic retinopathy (DR), a leading cause of blindness in type 1 and type 2 diabetics, is a complication of diabetes which produces damage to the blood vessels inside the retina. Diabetic retinopathy can have four stages: (1) mild nonproliferative retinopathy, wherein microaneurysms in the retina's blood vessels occur; (2) moderate nonproliferative retinopathy, wherein some blood vessels feeding the retina become blocked; (3) severe nonproliferative retinopathy, wherein many blood vessels to the retina are blocked, depriving several areas of the retina with their blood supply; and (4) proliferative retinopathy, wherein new, abnormal, thinwalled and fragile-walled blood vessels grow to supply blood to the retina, but which new blood vessels may leak blood to produce severe vision loss and blindness. Hemorrhages can occur more than once, often during sleep. Fluid can also leak into the center of the macula at any stage of diabetic retinopathy and cause macular edema and blurred vision. About 40 to 45 percent of Americans diagnosed with diabetes have some stage of diabetic retinopathy, and about half of the people with proliferative retinopathy also have macular edema.

Macular degeneration is a degeneration of the macular region of the retina in the eye. Degeneration of the macula causes a decrease in acute vision and can lead to eventual loss of acute vision. The wet form of macular degeneration is related to abnormal growth of blood vessels in the retina that can leak blood and can cause damage to photoreceptor cells. Age-related macular degeneration is a collection of clinically recognizable ocular findings that can lead to blindness. Macular degeneration is a group of diseases. There are two basic types of macular degeneration, including "wet" and "dry". In wet macular degeneration, there is an abnormal growth of new blood vessels (neovascularization). These new blood vessels break and leak fluid, causing damage to the central retina. This form of macular degeneration is often associated with aging. Approximately 85% of macular degeneration cases are dry macular degeneration. Vision loss can result from the accumulation of deposits in the retina called druzen, and from the death of photoreceptor cells in the retina. This process can lead to thinning and drying of the retina.

The findings of AMD include the presence of druzen, retinal pigment epithelial disturbance, including pigment clumping and/or dropout, retinal pigment epithelial detachment, geographic atrophy, subretinal neovascularization and disciform scar. Age-related macular degeneration is a leading cause of presently incurable blindness, particularly in persons over 55 years of age. Approximately one in four persons age 65 or over have signs of age-related maculopathy, and about 7% of persons age 75 or over have advanced macular degeneration with vision loss.

Druzen are opthalmoscopically visible, yellow-white hyaline excrescences or nodules of Bruch's membrane. Bruch's membrane lies beneath the retina and the adjacent retina pigment epithelium layer. Fat accumulates in Bruch's membrane with age and may contribute to the formation of druzen. Druzen can occur in two forms. One form comprises hard, small (less than about 60 micrometers in diameter) objects which do not increase with age and which do not predispose to macular degeneration. Another form comprises soft, large (more than about 63 micrometers in diameter) objects which enlarge and become confluent with age. The soft, large druzen may predispose to macular degeneration, and are commonly seen in eyes of people with advanced macular degeneration in at least their other eye.

Druzen may be metabolic waste products from various layers of the retina such as from the retina, retina pigment epithelium, and choriocapillaris. Druzen may be yellow, white, gray, retractile, and/or pink. Druzen may be small, medium or large in size. Druzen may be regular or irregular, or symmetrical or asymmetrical in shape. A patient who has druzen and who suffers complications in one eye may suffer no complications in the other eye. Complications may comprise one or more conditions selected from the group consisting of retina pigment epithelium atrophy, choroid neovascularization, retina detachment serous, and retina detachment hemorrhagic. Druzen may affect contrast sensitivity, and may reduce the eye's ability to see sufficiently to allow a person to read in dim light or to see sufficient detail to permit a person to drive an automobile safely at night.

A contributing and indicating factor of advanced macular degeneration is neovascularization of the choroid tissue underlying the photoreceptor cells in the macula. Healthy mature ocular vasculature is normally quiescent and exists in a state of homeostasis in which a balance is maintained between positive and negative mediators of angiogenesis in development of new vasculature. Macular degeneration, particularly in its advanced stages, is characterized by the pathological growth of new blood vessels in the choroid underlying the macula. Angiogenic blood vessels in the subretinal choroid can leak vision obscuring fluids, leading to blindness.

The major causes of blindness in the United States are glaucoma, AMD, cataracts, DR, and retinitis pigmentosa (RP) which translates into more than 38 million citizens having some form of an age related eye disease. In developed countries, cataracts are routinely surgically removed and vision is restored with the insertion of an artificial lens. There are no cures for most forms of the other blinding diseases, the severity of which increases with age and dramatically decreases the quality of life for these patients. Even for patients with an inherited blindness, such as RP, vision worsens with age. Nearly 1 out of 3 individuals over the age of 75 will develop some form of AMD and with the aging of the "Baby Boomers" generation, this means a dramatic increase in patient numbers. Nearly 200,000 individuals in the USA develop AMD each year. About 2 million Americans over the age of 40 have significant vision loss due to AMD while an additional 8 million have a high risk of vision loss. DR has some symptoms very similar to wet AMD including neovascular growth in the eye and subfoveal macular edema. About 4 million Americans age 40 and older have DR and >80% of patients who have diabetes for more than ten years will develop DR. Further, because Native American Indians develop diabetes at a much higher rate than the general population, DR is becoming a progressively increasing problem in states such as Oklahoma which have large numbers of Native Americans. The annual economic cost to the USA for adult vision loss is major at about $50 billion per year.

As noted above, AMD is classified roughly into two categories based on the absence or presence of choroidal neovascularizations which grow into the eye. Most patients have the dry form (85%) whereas about 15% have the wet form. The dry form is characterized by the accumulation of debris (druzen) between the retinal pigment epithelia and Bruch's membrane which effectively eliminates the benefits of the choroidal blood supply to the adjacent photoreceptor cells. The dry form can lead to the wet form, but optionally may not, and patients may still retain some retinal function throughout life. In the wet form, the presence of sub-macular neovascular vessels leads to retinal edema, ruptured blood vessels, the death of the cones in the macula and eventual blindness. Current therapeutic treatments for wet AMD involve intravitreal injections of monoclonal antibodies against Vascular Endothelial Growth Factor (VEGF) every 6-8 weeks. There are no treatments which have proven successful for dry AMD. Recently, a subform of AMD was recognized, called Retinal Angiomatous Proliferation (RAP), in which neovascular lesions occurred within the photoreceptor cell layer as a result of neovessels growing from the retinal vasculature through the photoreceptors, the RPE and Bruch's membrane where they joined choroidal neovascular tufts. These patients represent about 15% of the vascular form of AMD. It is an object of the present invention to develop a therapeutic treatment for blinding diseases, such as RAP.

Mammalian cells produce cellular energy in mitochondria by using oxygen to metabolize molecular substrates. The vast majority of the products of this oxidative metabolism are beneficial while about 3% are highly toxic compounds such as singlet oxygen, the hydroxide ion, and hydrogen peroxide. These Reactive Oxygen Species (ROS) can react with and damage almost any type of molecule within the cell including proteins, DNA, RNA and lipids. Another major source of intracellular ROS is NADPH oxidase which activates the STAT3 pathway which upregulates retinal VEGF. The normal antioxidant cellular defenses against ROS include catalytic proteins such as superoxide dismutase, heme oxygenase and thioredoxin as well as small molecules like glutathione, and NADPH. Oxidative stress occurs when the level of ROS exceeds the ability of the cells' antioxidant defenses to scavenge or destroy them. Because of the close proximity of the intra-mitochondrial components to the ROS, it is not surprising that they bear the brunt of damage from ROS and with decreased oxidative phosphorylation they produce less energy but more ROS.

As indicated herein, there are many diseases which result in the programmed cell death of photoreceptor cells and blindness. These include illnesses which are known to be inherited such as retinitis pigmentosa as well as many which have a genetic component but which may be environmentally induced or are of questionable origin such as diabetic retinopathy and AMD. Interestingly, irrespective of the primary cause, all of these diseases are thought to share some common nodes, including oxidative stress caused by a chronic or acute rise in ROS and apoptosis. The retina has the highest rate of oxygen metabolism, is constantly bombarded with photons of light, and is therefore exposed to a higher concentration of ROS than any other tissue of the body. Neurodegeneration within the retina is not unlike neurodegeneration within other areas of the central nervous system. Even in the albino rat model of light-induced degeneration of photoreceptor cells, initiation of apoptosis proceeds through the intracellular production of ROS. Strong evidence that oxidative damage is a primary cause of AMD was recently presented by Hollyfield et al. ("Oxidative damage-induced inflammation initiates age-related macular degeneration', Nat. Med. 2008; 14:194-198).

DETAILED DESCRIPTION OF THE INVENTION

Figure 1:
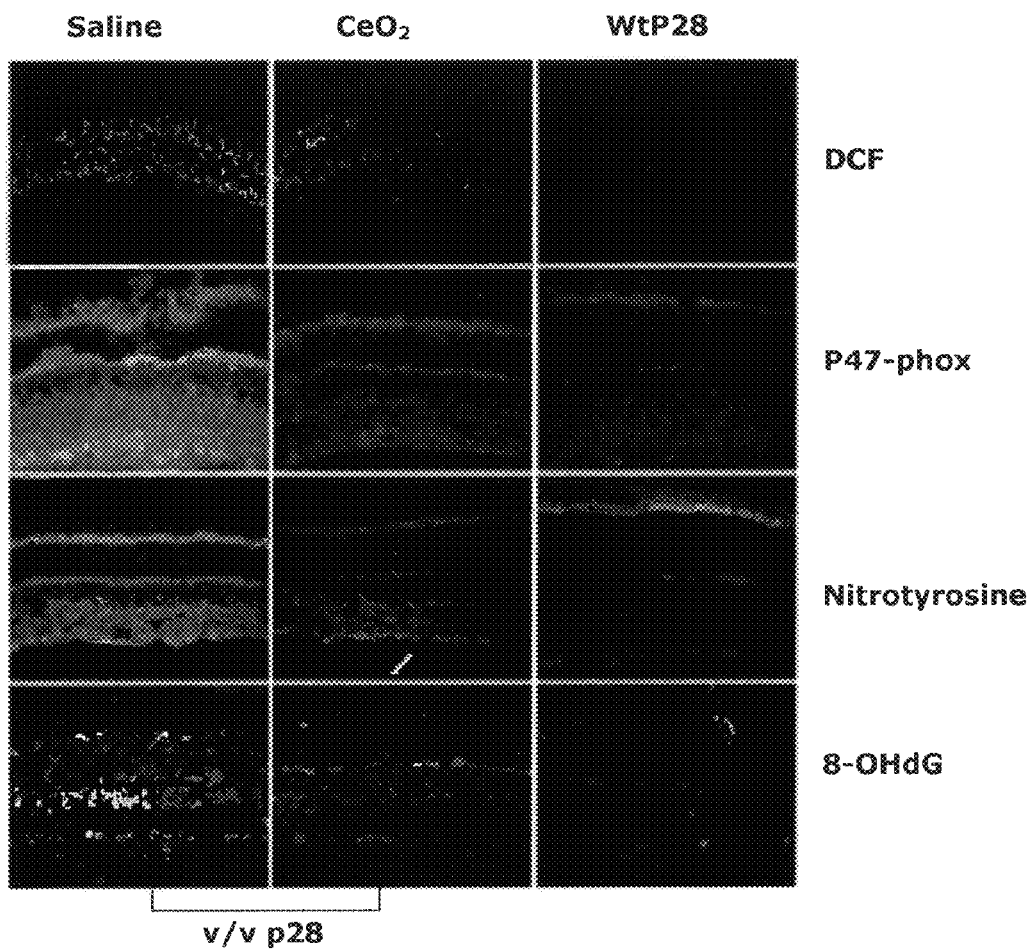
FIG. 1 shows photomicrographs of results from four assays for ROS and ROS-induced changes in VLDLr Knock Out (VLDLr KO) mouse retinas.

The present invention provides methods for reducing, treating, reversing, or inhibiting neovascularization in a tissue of a mammalian subject having a pathological condition involving neovascularization by in vivo administration of nanoceria particles (cerium oxide nanoparticles) in the subject. The method of the invention is useful, for example, for reducing, treating, reversing or inhibiting neovascularization in pathological conditions associated with ocular tissue such as the retina, macula or cornea; in skin; in synovial tissue; in intestinal tissue; or in bone. In addition, the method of the invention is useful for reducing, reversing or inhibiting neovascularization in neoplasms (tumors), which can be benign or malignant and, where malignant, can be metastatic neoplasms. As such, the invention provides compositions, which contain nanoceria particles and are useful for reducing, reversing, or inhibiting angiogenesis associated with such pathological condition in a mammalian subject.

The pathological conditions treated by the method of the invention include, but are not limited to, those of: the eye, such as diabetic retinopathy or macular degeneration; the skin, such as a hemangioma or psoriasis; a joint, such as rheumatoid arthritis or osteoarthritis; or the intestine, such as Crohn's disease or ulcerative colitis; or can be a tumor, which can be benign or malignant.

The present invention further provides methods of reducing, treating, reversing or inhibiting neovascularization (angiogenesis) in a tissue in an individual, by administering to the individual the nanoceria particles of the invention, thereby reducing or inhibiting angiogenesis in the tissue in the individual and, consequently, reducing the severity of the pathological condition exhibiting the angiogenesis. The condition can be any pathological condition associated with angiogenesis, including a neoplasm, which can be a malignant neoplasm, for example, a carcinoma such as breast carcinoma, colon carcinoma, ovarian carcinoma or pancreatic carcinoma, or a sarcoma, mesothelioma, teratocarcinoma, an astrocytoma, glioblastoma, or other neoplasm, including a metastatic malignant neoplasm. The agent can be administered by various routes, for example, intravenously or directly into the region to be treated, for example, directly into a neoplastic tumor; via eye drops or intravitreal injection, where the pathological condition involves the eye; or intrasynovially, where the condition involves a joint, or via other methods as discussed elsewhere herein.

Without wishing to be bound by theory, it is believed that in the present invention, the reduction, reversal, or inhibition of neovascularization in pathological conditions of ocular tissue such as retina, macula or cornea; of skin such as occurs with psoriasis; of synovial tissue; of bone; or of intestinal tissue; or of benign or malignant neoplasms occurs by reducing the reactive oxygen species (ROS) in the tissue.

The term "pathological condition" is used broadly herein to mean any abnormal physical or physiological condition characterized, at least in part, by neovascularization. Such pathological conditions include neoplasms, ocular diseases such as diabetic retinopathy and macular degeneration associated with neovascularization, skin diseases such as psoriasis and hemangiomas, gingivitis, arthritic conditions such as rheumatoid arthritis and osteoarthritis, and inflammatory bowel diseases.

The term "neoplasm" is used broadly herein to mean any new, pathological tissue growth. For purposes of the present invention, a neoplasm generally results in the formation of a tumor, which is characterized, in part, by angiogenesis. A neoplasm can be benign, for example, a hemangioma, glioma, teratoma, and the like, or can be malignant, for example, a carcinoma, sarcoma, glioblastoma, astrocytoma, neuroblastoma, retinoblastoma, and the like. The term "tumor" is used generally to refer to a benign or malignant neoplasm, and the term "cancer" is used generally to refer to a malignant neoplasm, which may or may not be metastatic. Malignant neoplasms that can be treated using a method of the invention include, for example, carcinomas such as lung cancer, breast cancer, prostate cancer, cervical cancer, pancreatic cancer, colon cancer and ovarian cancer; and sarcomas such as osteosarcoma and Kaposi's sarcoma, provided the neoplasm is characterized, at least in part, by angiogenesis.

An individual to be treated using a method of the invention can be any individual exhibiting a neovascularization associated with a pathological condition and, therefore, can be, for example, a vertebrate such as a mammal, including a human, other primate, dog, cat, horse, cow, sheep, or goat or any other mammal, particularly a commercially important animal or a domesticated animal and any other animal subject to diseases similar to those described herein.

Treatment using the methods of the present invention is considered to be successful when adverse clinical signs or symptoms associated in the subject with the pathological condition being treated are reduced, reversed, inhibited, or otherwise ameliorated. A reduction in the severity of a pathologic condition can be detected by various methods, including routine clinical tests such as blood tests, which can used to determine relevant enzyme levels or circulating antigen or antibody; imaging tests, which can be used to detect a decrease in the growth rate or size of a neoplasm; or an ophthalmic procedure, which can be used to identify a reduction in the number of blood vessels in the retina of a diabetic patient. Such clinical tests are selected based on the particular pathological condition being treated. A reduction in the severity of a pathological condition also can be detected based on comments made by the patient being treated, for example, that a patient suffering from arthritis feels less pain or has greater joint mobility, or that a patient with diabetic retinopathy or with macular degeneration due to neovascularization can see more clearly, or the like.

The nanoceria particle composition of the invention generally will be in the form of a pharmaceutical composition comprising the nanoceria particles and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

The total amount of the nanoceria composition can be administered to a subject as a single dose, over a relatively short period of time, or can be administered using a treatment protocol in which multiple doses are administered over a more prolonged period of time. The concentration and quantity of the nanoceria required in the treatment protocol depends on many factors including the age and general health of the subject as well as the route of administration, the number of treatments to be administered.

The nanoceria of the present invention which are useful for reducing or inhibiting angiogenesis or a pharmaceutical composition thereof containing the nanoceria can be used for treating any pathological condition that is characterized, at least in part, by neovascularization. The nanoceria can be administered by various routes including, for example, parenterally, including intravenously, intramuscularly, subcutaneously, intraorbitally, intracapsularly, intrasynovially, intraperitoneally, intracisternally or by passive or facilitated absorption through the skin using, for example, a skin patch or transdermal iontophoresis. Furthermore, the composition can be administered by injection, intubation, via a suppository, orally or topically, the latter of which can be passive, for example, by direct application of an ointment or powder containing the composition, or active, for example, using a nasal spray or inhalant. The pharmaceutical composition also can be incorporated, if desired, into liposomes, microspheres or other polymer matrices as discussed elsewhere herein.

In one embodiment the present invention comprises therapeutic treatments which eliminate the leaky neovessels, choroidal neovascularization and vascular lesions within the retinas of mammals with RAP and other ocular diseases characterized by neovascularization. The present therapeutic regimes also slow the progression of photoreceptor cell death, for example in all forms of AMD and DR. These treatments will dramatically improve the quality of life for millions of Americans and correspondingly reduce the $50 billion annual economic cost to the USA.

The present invention in particular relates to methods of treatment of macular degeneration associated with subretinal neovascularization and a proliferation of neovascular tissue in the eye of a mammalian subject, and to methods of inhibiting or substantially reducing the rate of subretinal neovascularization and proliferation of neovascular tissue in the eye associated with macular degeneration.

The present invention also relates to methods of treatment of diabetic neuropathy, especially diabetic retinopathy associated with neovascularization, and to methods of inhibiting or substantially reducing the rate of proliferation of neovascular tissue in the eye associated with diabetic neuropathy Examples of cerium oxide nanoparticles that may be used in the present invention include, but are not limited to, those described in U.S. Pat. Nos. 7,347,987 and 7,504,356 (each of which are expressly incorporated by reference herein) and include, but are not limited to, cerium oxides having the formulas $CeO_2$ and $Ce_2O_3$.

The nanoceria particles of the composition are administered in one embodiment at concentrations of 1 nM to 1000 μM, or from 1 nM to 100 μM, or from 1 nM to 10 μM, or from 1 nM to 1 μM, or from 1 nM to 100 nM, or from 1 nM to 50 nM, or from 1 nM to 10 nM, or from 10 nM to 10 μM, or from 100 nM to 10 μM. More particularly, the cerium oxide particles of the present invention are further characterized as ultra-fine and are preferably in a size range of from approximately 1 nanometer in diameter to approximately 10 nanometers in diameter; more preferably from approximately 1 nm to approximately 7 nm.

Examples of various methods of administering therapeutic compositions to the eye, and which may be used to administer the nanoceria of the present invention, are described, for example, in U.S. Pat. No. 7,442,686, the entirety of which is hereby expressly incorporated herein by reference.

For example, the nanoceria particles may be administered by direct injection into the eye, intravenous, intraperitoneal, intramuscular, oral or topically on the eye or skin. The nanoceria will reduce damage to the eye caused by angiogenesis ocular pathological conditions including, but not limited to, glaucoma, diabetic retinopathy, inherited retinal degeneration (for example, RP), AMD, retinal detachment or any disease or event which involves production of ROS, neovascularization, for example, including retinopathy of prematurity (ROP), neovascular glaucoma, macular edema, Sickle Cell retinopathy, choroidal neovascularization, retinal vascular diseases, and ocular oncology. These particles will preserve and prolong vision when administered in vivo.

Administration of the nanoceria compositions of this invention is preferably by injection, such as by injection into an eye, preferably into a blood vessel that supplies blood to the eye or by microinjection into the macula by first penetrating the sclera, by topical application such as to a tissue of the eye such as the cornea or sclera, or by implantation such as by controlled release from a depot or implant comprising a pharmaceutically acceptable matrix or pharmaceutically acceptable carrier, which depot or implant is located proximal to the tissue of the eye, preferably proximal to or embedded into tissue comprising the posterior portion of the eye. A therapeutically effective amount of the composition of this invention can be delivered to the choroid and retina proximal to the macula of the eye to retard the growth of blood vessels that lead to macular degeneration in the eye.

In one aspect, therapeutic compositions of this invention can be administered to the eye or other areas of the body by a number of techniques including by use of medical devices and methods of administration known in the art, such as for example those described in U.S. Pat. Nos. 6,397,849; 6,299,895; 5,770,589; 5,767,079; 5,707,643; 5,632,984; 5,443,505; 5,399,163; 5,383,851; 5,273,530; 5,064,413; 4,941,880; 4,790,824; 4,596,556; 4,487,603; 4,486,194; 4,475,196; 4,447,224; 4,447,233; and 4,439,196, each of which is expressly incorporated herein by reference in its entirety. Many other methods of administration such as a single or multiple implant and/or biodegradable matrix composition for controlled release the nanoceria of this invention, an implantable hydrogel matrix which can be biodegradable, an injectable delivery system such as a liposome suspension, injection methods such as comprising a needle less syringe or cannula or needle and syringe, poorly water soluble and biodegradable carriers, and delivery routes that are applicable to administer a drug to the eye and to blood vessels that feed blood to the eye can be used with the compositions of this invention.

For example, the present invention can be delivered by a variety of techniques to the macula region of the eye, preferably to the posterior segment of the eye proximal to the macula. Examples of such techniques include: (a) use of a sterile, pharmaceutically acceptable biodegradable scleral plug which comprises nanoceria and optionally a pharmaceutically acceptable biodegradable matrix such as a polylactic acid or polyglycolic acid or a copolymer of lactic acid and glycolic acid, which plug can be inserted into the eye via an incision in the sclera; (b) use of an implant comprising nanoceria of this invention and optionally a pharmaceutically acceptable biodegradable matrix wherein the sclera is cut to expose the suprachoroid and wherein the implant is placed into a suprachoroidal space from which implant the nanoceria are released, for example, into the vitreous region of the eye; (c) use of intravitreal injection into the vitreous body of a pharmaceutical composition comprising nanoceria and a sterile aqueous carrier; (d) injection or infusion via a flexible cannula that can be inserted through the posterior sclera and down into the subretinal space at the posterior region of the eye; and (e) by injection of a pharmaceutical composition comprising nanoceria and a pharmaceutically acceptable carrier into an avascular region of the sclera to form a depot comprising nanoceria within the scleral layer and from which the nanoceria can diffuse to the macula, choroid layer, and/or retina.

In one aspect, a pharmaceutical compositions used in the present invention can comprise a pharmaceutically acceptable carrier selected from the group consisting of poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid, polycaprolactone, polyvalerolactone, poly(anhydrides), copolymers of polycaprolactone with polyethylene glycol, copolymers of polylactic acid with polyethylene glycol, polyethylene glycol; fibrin, Gelfoam™ (which is a water-insoluble, off-white, nonelastic, porous, pliable gel foam prepared from purified gelatin and water for injection), and combinations and blends thereof. Copolymers can comprise from about 1% to about 99% by weight of a first monomer unit such as ethylene oxide and from 99% to about 1% by weight of a second monomer unit such as propylene oxide. Blends of a first polymer such as gelatin and a second polymer such as poly-L-lactic acid or polyglycolic acid can comprise from about 1% to about 99% by weight of the first polymer and from about 99% to about 1% of the second polymer.

The term "pharmaceutically acceptable carrier" or "adjuvant" and "physiologically acceptable vehicle" and the like are to be understood as referring to an acceptable carrier or adjuvant that may be administered to a subject, together with nanoceria of this invention. Further, as used herein "pharmaceutically acceptable carrier" or "pharmaceutical carrier" are known in the art and include, but are not limited to, 0.01-0.1 M solutions and preferably 0.05 M phosphate buffer, or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount of nanoceria (dose) effective in treating a patient, having, for example, a site of neovascularization. It is also to be understood herein that a "pharmaceutically effective amount" may be interpreted as an amount giving a desired therapeutic effect, either taken in one dose or in any dosage or route or taken alone or in combination with other therapeutic agents.

Advanced wet AMD is a disease of the eye which comprises neovascularization of the choroid tissue underlying the photoreceptor cells in the macula. As noted above, AMD, particularly in its advanced stages, is characterized by the pathological growth of new blood vessels in the choroid underlying the macula. Angiogenic blood vessels in the subretinal choroid can leak vision obscuring fluids, leading to blindness.

In one aspect, diseases of the eye which exhibit neovascularization proximal to the retina such as wet AMD, retinitis pigmentosa, Stargardt's Disease, diabetic retinopathy, hypertensive retinopathy, and occlusive retinopathy can be treated to reduce the rate of neovascularization by administration of a composition of this invention comprising nanoceria having angiogenesis inhibiting activity.

The compositions of the present invention when administered to the eye or to blood vessels that feed into the eye of a patient can be useful to treat ocular diseases such as, but not limited to, wet AMD, RP, Stargardt's Disease, DR, hypertensive retinopathy, and occlusive retinopathy by reducing the rate of formation of neovascularization and thereby slow the progress of the disease. The rate of neovascularization which occurs in such a disease in a patient is preferably reduced by administration of the nanoceria of this invention to 90%, more preferably to 50%, even more preferably to 25%, even more preferably to 10%, even more preferably to 5%, even more preferably to 1%, and most preferably to 0.1% or less of the rate of neovascularization which occurs in such a disease in the absence of administration of the nanoceria of this invention (i.e., in an untreated patient).

Administration of a pharmaceutical composition comprising the nanoceria of this invention to a subject in need of treatment for a disease of the eye such as macular degeneration, retinitis pigmentosa, Stargardt's Disease, diabetic retinopathy, hypertensive retinopathy, and occlusive retinopathy can substantially reduce or prevent angiogenesis associated with subretinal neovascularization, choroid neovascularization underlying the macula, and a proliferation of neovascular tissue in the subretinal choroid proximal to the macula in an eye in a mammalian subject.

The method can be useful as a prophylactic treatment to prevent further onset or progression of macular or retinal degeneration in an eye that exhibits symptoms of a disease of the eye such as macular degeneration, retinitis pigmentosa, Stargardt's Disease, diabetic retinopathy, hypertensive retinopathy, and occlusive retinopathy. In another aspect, the method can be useful as a prophylactic treatment to prevent the deposition of druzen and the death of photoreceptor cells in the macula or elsewhere in the retina. In one aspect of the invention, the method can prevent the death of photoreceptor cells (which photoreceptor cells are also herein referred to as photoreceptors) in the eye of a subject by acting on intracellular mechanisms of the regulation of cell death. The method can also be useful to prevent onset or progression of macular degeneration in an eye that does not exhibit vision-obscuring symptoms of macular degeneration, especially in an eye of a patient whose other eye does exhibit vision-obscuring symptoms of macular degeneration.

In another aspect of this invention, a method of treatment of a disease of the eye such as macular degeneration, retinitis pigmentosa, Stargardt's Disease, diabetic retinopathy, hypertensive retinopathy, and occlusive retinopathy comprises administration such as by injection or implantation (or other method described herein) into tissue proximal to the eye of a therapeutically effective amount of nanoceria of this invention, or of a sterile pharmaceutical composition of this invention suitable for injectable administration and comprising nanoceria of this invention and a carrier suitable for injectable use (e.g., sterile, sterilizable, and isotonic with blood), which can prevent or delay the onset of angiogenesis associated with subretinal neovascularization, choroid neovascularization underlying the macula, and a proliferation of neovascular tissue in the subretinal choroid proximal to the macula in an eye of a patient.

The invention further comprises a combination therapy wherein a VEGF inhibitor may be administered in combination with the present nanoceria therapy. The nanoceria may be administered with a cytotoxic agent, a chemotherapeutic agent or a growth inhibitory agent can be administered to the subject together in a single dosage composition such as a combined formulation, or each agent can be administered in a separate dosage formulation. Where separate dosage formulations are used, the nanoceria of the invention and one or more additional agents can be administered concurrently, or at separately staggered times, i.e., sequentially. The therapeutic methods of the invention may also be combined with other agents or medical procedures used for treatment of eye disorders or other pathological conditions expressing neovascularization.

Nanoceria particles are contemplated herein for use in preventing blindness due to a variety of diseases including, but not limited to, macular degeneration, hereditary retinitis pigmentosa, glaucoma, diabetes, and retinal detachment.

Investigations of nanocrystalline cerium oxide (e.g., $CeO_2$ and $Ce_2O_3$) nanoparticles (nanoceria) have revealed that its lattice constant increases with decreasing nanoparticle size. This has been attributed to an increase in oxygen vacancies in the crystal structure. This suggests that the migration enthalpy of the oxygen vacancy in $CeO_2$ is smaller at the nanoscale. Additionally, at the nanoscale, the surface area of $CeO_2$ particles is dramatically enlarged in relation to its volume which increases oxygen exchange and redox reactions. Thus, oxygen vacancies are likely to form more readily at the nanoscale.

It is believed that nanoceria, owing to their chemical and physical structure, can protect cells from ROS or free-radical-induced damage. This is especially supported by the demonstration that nanoceria have catalytic activities like those of two major anti-oxidative enzymes, super oxide dismutate and catalase. The "defects" in the nanoceria particles can act as chemical spin traps similar to nitrosone compounds, currently used as biological antioxidants. It is believed that the nanoceria act as free-radical scavengers by switching between the +3 and +4 valence states via various surface chemical reactions and one $CeO_2$ nanoparticle may offer many sites of spin-trap activity, whereas current pharmacological agents offer only a few per molecule. Additionally, the lattice defects in nanoceria can regenerate and do not necessarily require repetitive dosages as seen with the use of dietary supplements of antioxidants such as vitamins C and E. It was previously demonstrated that the intravitreal injection of nanoceria, which catalytically scavenge ROS, prevents light damage and blindness in albino rats. Herein we demonstrate (as described below) that nanoceria catalytically destroy ROS in the retinas of VLDLr Knock Out mice which in turn prevent oxidative stress and ROS induced damage such as increases in VEGF, choroidal neovascularization, retinal vascular lesions, degeneration of photoreceptor cells and the subsequent loss of vision.

Experimental

The VLDLr KO Mouse Model:

The Very Low Density Lipid Receptor Knock Out mouse (VLDLr KO), (see Heckenlively et al., "Mouse model of subretinal neovascularization with choroidal anastomosis". *Retina* 2003; 23: 518-522), is an outstanding animal model for AMD and in particular for RAP (Retinal Angiomatous Proliferation) in which there is a progressive increase in retinal VEGF and VEGF-induced vascular proliferation within the photoreceptor cell outer nuclear layer as well as an accumulation of lipid particles with degeneration of Bruch's membrane. This mouse also exhibits subretinal choroidal neovascularization. Oxidative stress in the VLDLr KO mouse has also been shown to be associated with a low antioxidant capacity in its mitochondria. The overall phenotype is very similar to that associated with a subset of AMD patients who have Retina Angiomatous Proliferation (RAP). VEGF is responsible for angiogenesis and vasculature formation in the eye and numerous strategies have been designed to inhibit its activity in many diseases, including AMD and cancer. Currently, the only effective therapy for wet AMD is the intravitreal injection, every 4-6 weeks, of monoclonal antibodies against VEGF, aptamers which inhibit VEGF activity or soluble receptors for VEGF which act as "VEGF traps". Our recently published data (Li et al., "Biochemical alterations in the retinas of very low-density lipoprotein receptor knockout mice: an animal model of retinal angiomatous proliferation". *Arch Opthalmol* 2007; 125: 795-803), demonstrated the rise in VEGF in the ONL of the retina, the developmental increase in illicit blood vessels and the increase in pro-inflammatory enzymes prior to vascularization. We hypothesized herein that nanoceria, through scavenging of ROS, can inhibit the rise in VEGF, the subsequent angiogenesis and vascular lesions in the retina and the eventual photoreceptor cell death. Data provided herewith support this assertion.

In this mouse model (VLDLr KO) for macular degeneration, blood vessels form and grow from the retinal vasculature through the choroid and retinal pigment epithelium layer. In some forms of macular degeneration and in diabetic retinopathy, the retinal blood vessels also become "leaky". As shown in the data below, administration of nanoceria particles prevents both choroidal neovascularization (CNV) and leakage of the retinal blood vessels.

We hypothesized that the nanoceria, by a mechanism involving the elimination of endogenously produced ROS, inhibit the mutant phenotype of the $VLDL_R$ −/− mouse. The phenotypic characteristics which were measured were: ROS and ROS-mediated damage in the retina; the illicit rise in Vascular Endothelial Growth Factor (VEGF); retinal vascular lesions; subretinal neovascularization; disruption of Bruch's membrane and the retinal pigment epithelium cell layer by choroidal neovascular tufts. Quantitative histology, using bright field microscopy on hematoxylin and eosin (H&E) stained retinal sections, were used to evaluate the morphological preservation of photoreceptor cells whereas retinal function was determined using electroretinography. VEGF levels in the retina were assayed with anti-VEGF immunoblots, ELISAs and immunocytochemistry whereas its mRNA were assayed by RT-PCR. Superoxide radicals in the retina were assessed using a hydroxyethidine assay whereas $H_2O_2$ were assayed with 2',7'-dichloro-dihydro-fluorescein-diacetate. ROS-induced damage were visualized with antibodies against products of ROS activity including acrolein, nitrotyrosine and 8-hydroxy-2-deoxy-guanosine. The effects of the nanoceria on neuroprotective pathways were analyzed by Western blots and cDNA micro arrays. We have established a vascular filling assay to visualize both the retinal vasculature and choroidal neovascularizations. Our new Olympus Zoom Fluorescence Microscope (MVX10) for macro to microfluorescence imaging enabled us to perform fluorescein angiography on the same live mouse and follow the development and/or regression of the choroidal neovascular tufts and the retinal vascular blebs and lesions on successive days for the same mouse. A major advantage of our current in vivo assays is that the data can be obtained within one week.

Effects on ROS and ROS-induced Damage

We first performed experiments to determine if there actually was an increase in ROS in the retina of the VLDLr KO mouse and if the nanoceria could reduce the ROS and the damage caused by them. In a cell, the three major sources of intracellular ROS are from 1) mitochondrial oxidative respiration, 2) NADPH-oxidase and 3) Nitrous oxide synthetase (NOS3). FIG. 1 shows representative data from four different assays (three mice for each condition for each assay) for ROS and ROS-induced changes. A single injection of saline or nanoceria (1 µl of 1 mM nanoceria) was given on P7 ($7^{th}$ day after birth) and three weeks later the retinas were collected. These data demonstrate that ROS and ROS-induced effects increase in VLDLr KO retinas and that the treatments with nanoceria decrease these characteristics. All settings for the fluorescence confocal microscope were constant within each of the assays.

The dihydrodichlorofluorescein assay (DCF) visualizes cellular oxidation by hydrogen peroxide, peroxynitrite and hydroxyl radicals. The data show very low levels of DCF in the normal retina (Wt p28), high levels of DCF in the saline injected VLDLr KO retina (v/v p28) and greatly reduced levels in the nanoceria ($CeO_2$) injected VLDLr retina KO.

A major source of intracellular ROS is from the enzyme NADPH Oxidase. Our data show that the intensity of staining for its activating subunit, P47, is greatly increased in the VLDLr KO retina vs the normal control but is reduced almost to control levels by injection of nanoceria.

Nitrotyrosine is a marker for the intracellular effects of Nitrous Oxygen Species. Our data show that the VLDLr KO retina stains very intensely whereas the retinas from control and nanoceria injected VLDLr KO mice show greatly reduced staining.

ROS-induced damage to DNA is reflected in the amount of 8-hydroxy-2'-deoxyguanosine (8-OH-dG) present. This assay requires digestion of the cryostat section with proteinase K which results in poor preservation of retinal morphology. However the data show that the nanoceria reduce the staining for 8-OHdG in the VLDLr KO retinas to near control levels.

VEGF—Western Data.

Figure 2:
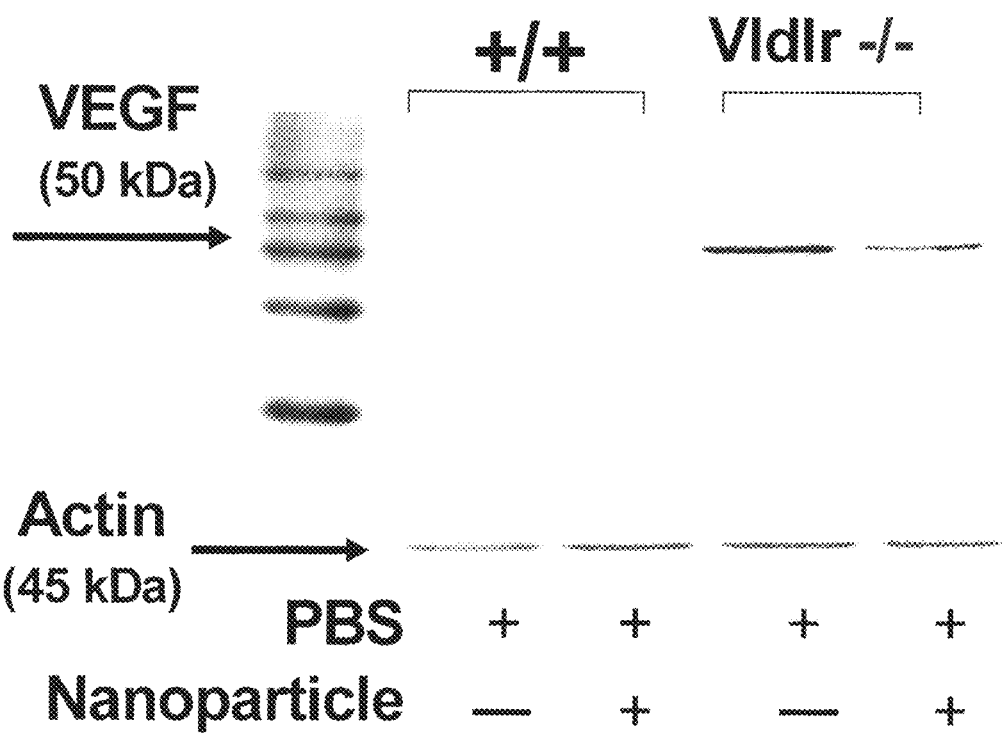
FIG. 2 is a schematic showing that nanoceria inhibit the rise in VEGF in retinas of VLDLr KO mice. Actin was stained as a load control.

Mice were injected intravitreally with either 1 µl of PBS or 1 ul of PBS plus nanoceria at postnatal P13 and the animals killed on P21. Retinas were homogenized, subjected to SDS-PAGE, and blotted to nitrocellulose. The bands were detected with primary and secondary antibodies and visualized with an HRP-DAB assay (FIG. 2). Wild type (+/+) retinas had barely detectable levels of VEGF with or without nanoceria. The VLDLr KO retinas had about an eightfold increase in VEGF compared to the +/+ retinas. However, the nanoceria injected VLDLr KO mice had about 60% less VEGF at day 21. These data indicate that VEGF increased in the VLDLr KO retinas due to ROS and that it decreased because of the nanoceria mediated decrease in ROS.

VEGF—Localization by Immunofluorescence.

Figure 3:
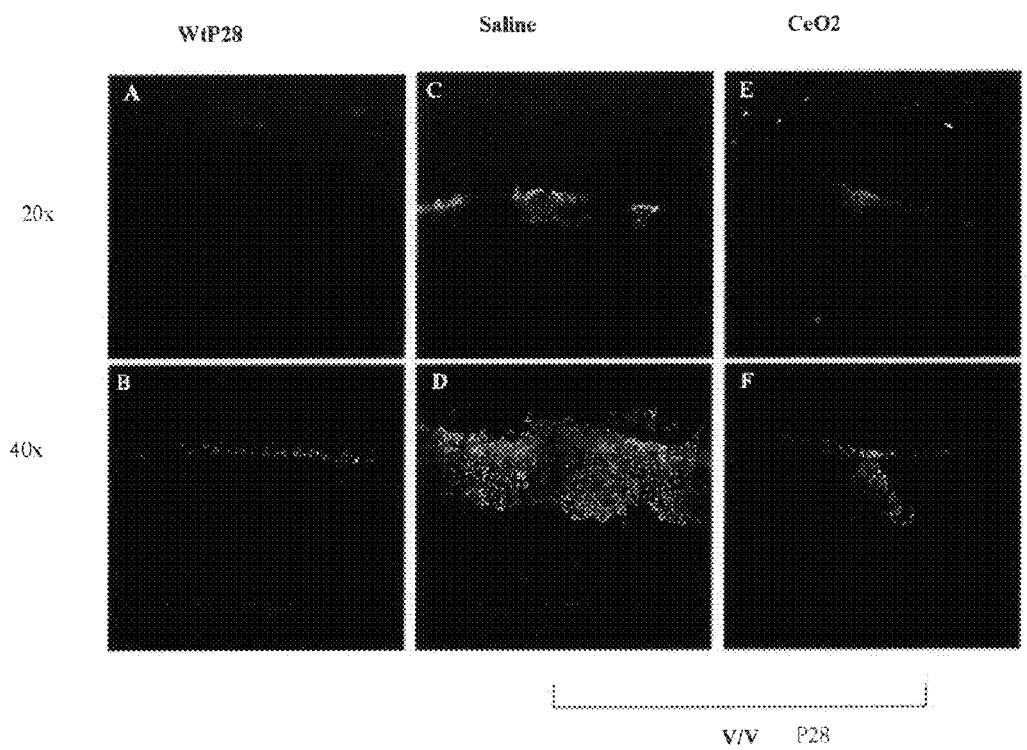
FIG. 3 shows immunofluorescence confocal photomicrographs of retinas to show localization of VEGF in retinas and effects of nanoceria thereon.

To determine where VEGF was localized in the Wild type and the VLDLr KO retinas and whether the nanoceria had any effect on the localization, Alexa green-conjugated secondary antibodies were used in combination with anti-VEGF primary immunoglobulins. The wild type mouse retinas (C57BL/6J) (FIG. 3A,B) had very little VEGF and it was localized to the outer segments of the retina. However, the pattern of labeling with anti-VEGF in the VLDLr KO retina (FIG. 3C,D) was heavy but discontinuous; predominantly in the outer and inner segments of photoreceptors; and especially in their perinuclear regions in the ONL adjacent to vascular lesions. The intensity of labeling progressively diminished as the distance from the lesion increased. The age-matched VLDLr mice, which had received an intravitreal injection (1 ul of 1 mM) of nanoceria on P7, had fewer vascular lesions and exhibited greatly reduced staining surrounding the remaining lesions (FIG. 3. E, F). Individual "optical sections" reveal uniform labeling of the cytoplasm surrounding the photoreceptor cell nuclei and inner segments which suggests that the VLDLr KO photoreceptor cells are making VEGF. Also, a single injection of the nanoceria at P7 inhibits the developmental increase in retinal VEGF for at least three weeks. These data demonstrate that the rise in retinal VEGF in the VLDLr KO retina is due to ROS and can be prevented by the scavenging activities of nanoceria.

Nanoceria Inhibit Development of "Neo" Leaky Retinal Vasculature in VLDLr KO Retinas.

Figure 4:
FIG. 4 shows micrographs of VLDLr KO retinal layers which show formation of new blood vessels ("bleb" at arrowheads). These blebs are reduced by nanoceria treatment.

The retina has two blood supplies, the retinal vasculature and the choroid. The VLDLr KO retina has problems with both systems. The retinal vasculature of the VLDLr KO mouse exhibits a developmental increase in "neo" vessels which are absent from control retinas suggesting the possibility that these vessels arise as a result of the increase in retinal VEGF and that the nanoceria can inhibit their development. To test this, we used fluorescein-conjugated Dextran to visualize the retinal vasculature and asked if an intravitreal injection of the nanoceria on P7 could inhibit the formation of these illicit blood vessels when visualized on P28. Representative images from such an experiment are shown in FIG. 4. With this assay, the larger vessels in the control C57 retinas (FIG. 4A) are very bright with the smaller vessels forming a less intensely labeled meshwork. Injection of nanoceria or saline has no effect on the normal retinal vasculature so that data is not shown. The VLDLr KO retinal vessels of saline injected (FIG. 4B) or uninjected (not shown) mice have brightly labeled newly formed vessels with coiled ends (appearing as "blebs") which project toward the RPE cells. The nanoceria injected VLDLr KO eyes (FIG. 4C) show greatly reduced numbers of these neovessels.

Nanoceria Inhibit Development of Choroidal Neovascular Tufts.

Figure 5:
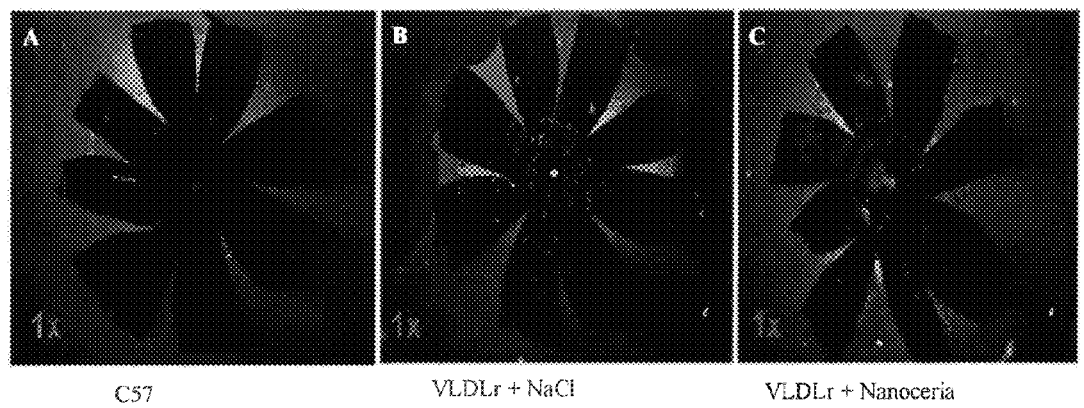
FIG. 5 shows cut and flattened eyecups of normal (C57) and VLDLr KO mice, with and without treatment with nanoceria.

The vascular filling assay also enables choroidal neovascular connections between the choroid and retina blood supplies to be visualized. In this case, after the retina has been removed the remaining RPE-sclera-choroid is "pie-cut" to allow flat mounting and placed with the RPE facing up (FIG. 5). The pigmented RPE prevent visualization of any of the choroidal vasculature in the normal C57 mouse (FIG. 5A) but the eyecup from the saline injected VLDLr KO mice (FIG. 5B) had numerous bright choroidal neovascular tufts which projected through the RPE cell layer. However, the eyes of the VLDLr KO mice which had been injected with nanoceria (FIG. 5 C) have far fewer choroidal neovascular tufts.

Vascular Lesions can be Quantified.

Figure 6:
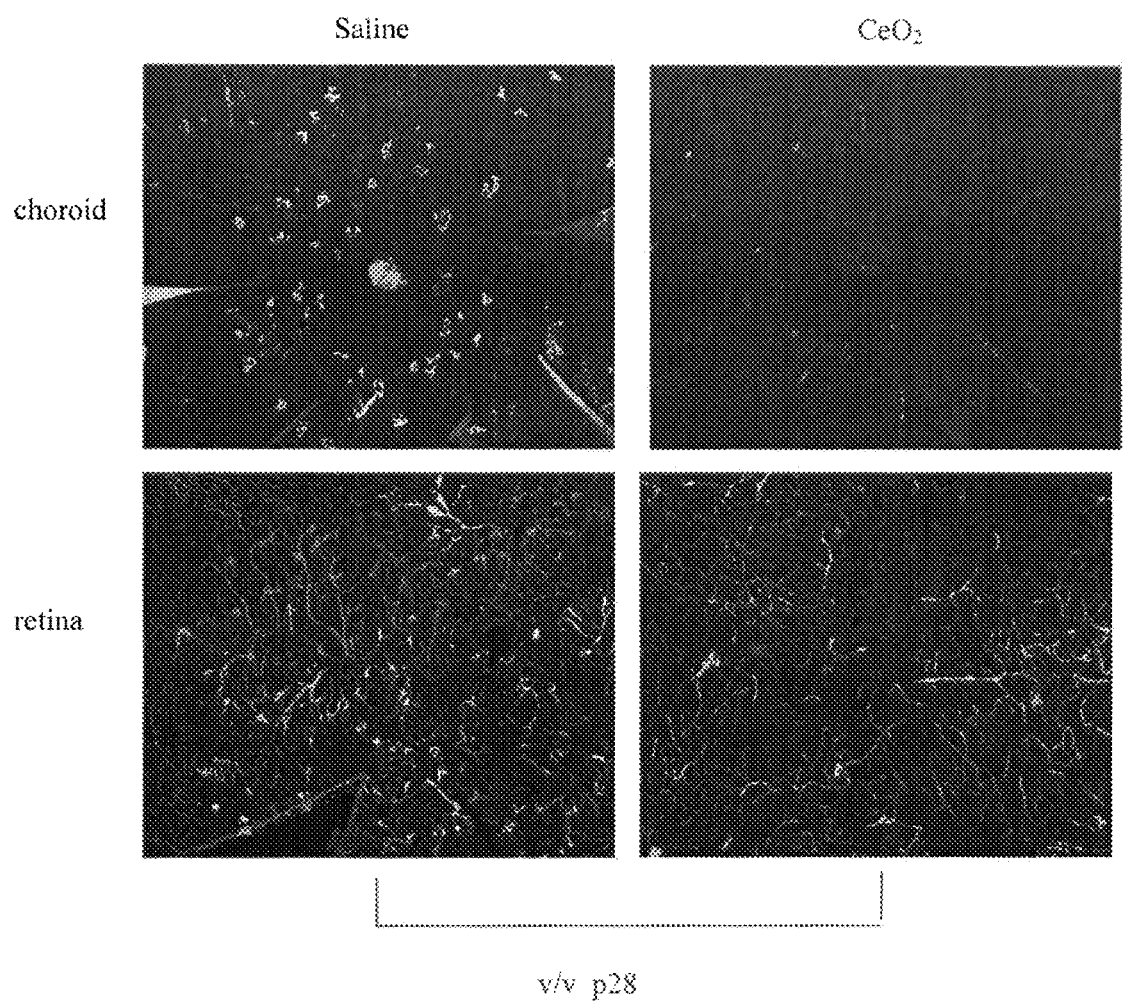
FIG. 6 shows micrographs of VLDLr KO vascular defects.
Figure 7:
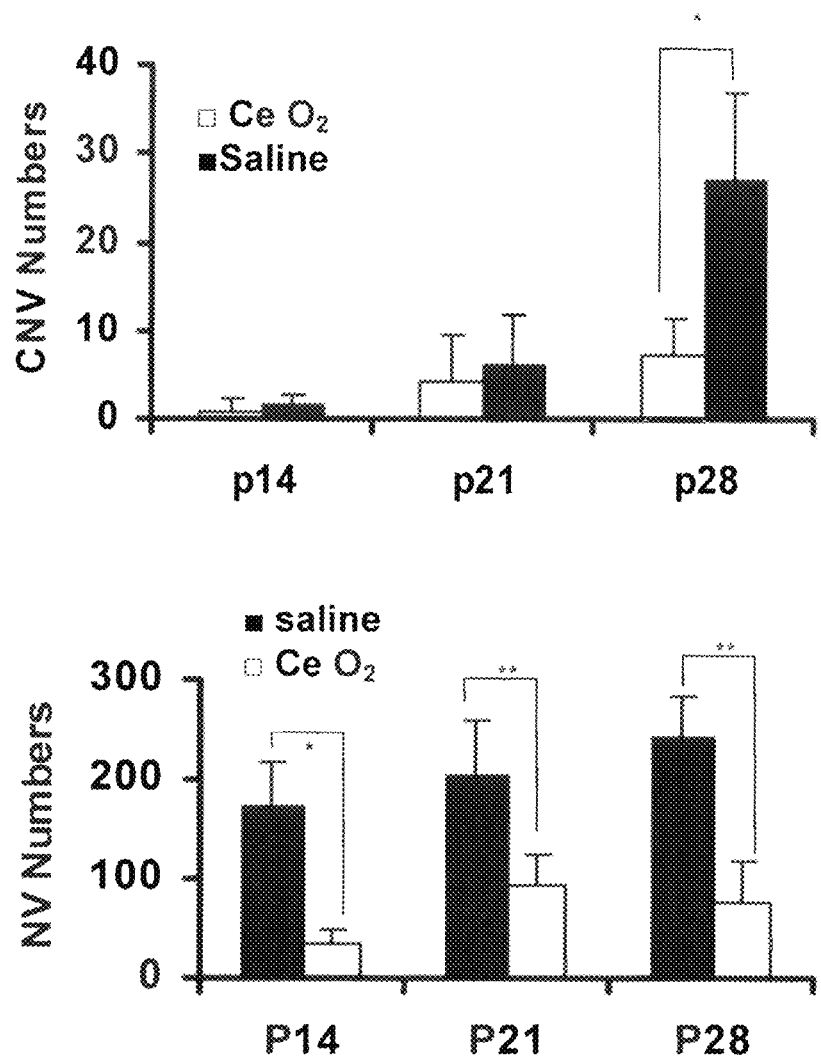
FIG. 7 is a graph showing the effects of treatment with nanoceria on numbers of choroidal tufts.

Because choroidal neovascular "tufts" and retinal neovascular "blebs" are readily visible, both can be quantified. The results of such an experiment are presented in FIG. 6 and FIG. 7 and demonstrate that the number of choroidal tufts present during development increases, especially by P28. The data also show that a single injection of nanoceria at P7 decreases the number of such tufts seen in P14, P21 and P28 VLDLr KO choroids. The confocal microscope shows the vascular lesions as "blebs" which are present in significant numbers even at P14 and progressively increase at P21 and P28. As with the tufts, the developmental appearance of the blebs is strongly inhibited by a single injection of nanoceria at P7. These data strongly support our hypothesis that ROS represents an important connection between the primary defect and the downstream effects which in the VLDLr KO mouse are vascular defects. These data also indicate that by counting blebs and tufts, the effectiveness of a therapeutic treatment can be evaluated. Therefore, dose response experiments can be done to determine the lowest dose of nanoceria that is most effective. This assay also enables a comparative analysis to be performed between nanoceria and other antioxidant agents.

Regression of Vascular Anomalies by Treatment with Nanoceria.

Figure 8:
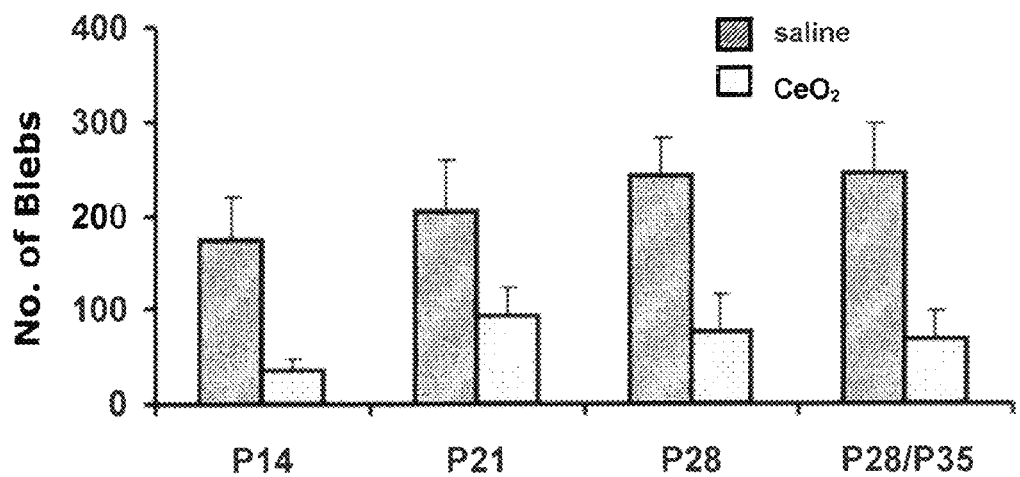
FIG. 8 is a graph showing that nanoceria treatment causes regression of retinal vascular lesions which were present prior to treatment.

Although these data were scientifically very important for our hypothesis, from a therapeutic perspective, the nanoceria would be much more useful if they could decrease or eliminate the vascular anomalies which were present prior to their injection. To examine this possibility, we added an experimental paradigm to that which is seen previously in FIG. 6. We also asked what would happen to the retinal blebs already present prior to injection. To answer this, mice were injected on day 28 and the vascular filling assay was done on day 35. The P28/35 data are shown in FIG. 8 and indicate that the retinal vascular lesions, blebs, have slightly increased in the saline injected mice but in the nanoceria injected mice the blebs have regressed to the same level as was found on P28 when the mice were injected at P7. Similar data was obtained when the CNV blobs were counted (data not shown). These are especially important observations because they indicate that the vascular blebs and blobs present at the time of injection on day 28 are dependent on the presence of ROS and their downstream effects. Therapeutically this means the nanoceria are effective in subjects which already have vascular anomalies. These data also indicate that the continued presence of these illicit new blood vessels in the retinal vasculature requires the continual production of ROS and that the "assay" for therapeutic effects can be done within a week.

Figure 9:
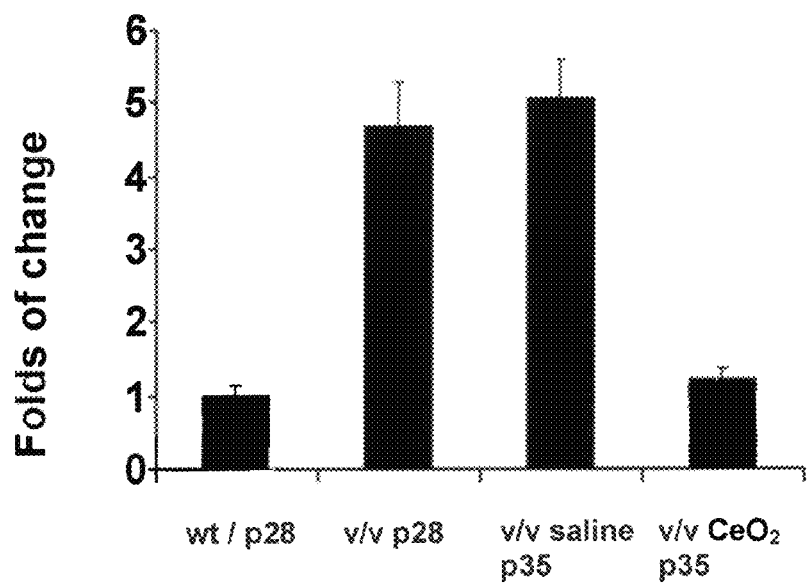
FIG. 9 is a graph showing that nanoceria downregulate VEGF in mature VLDLr KO retinas.

In a separate parallel experiment, VEGF was quantified using densitometry of anti-VEGF bands on immunoblots. The data (FIG. 9) show that the injection of nanoceria at day 28 into a mature mouse decreases by day 35 to the amount of retinal VEGF to that found in normal retinas.

Results with this VLDLr KO mouse model are striking. These data demonstrate that the nanoceria down regulate retinal VEGF, inhibit the formation of new leaky blood vessels in the retinal vasculature and inhibit choroidal neovascularization. Our assays also enable dose response data to accurately evaluate the effectiveness of different preparations of nanoceria. In addition, because the nanoceria were also shown to be therapeutic even when administered after the illicit retinal vessels have formed, we can now directly compare the efficacy of the nanoceria over time with conventional treatments using anti-VEGF antibodies which are currently injected intravitreally every 4-6 weeks for patients with wet AMD. It is contemplated that nanoceria treatments are effective in macular edema and diabetic retinopathy.

Our data demonstrate four major points. The first is that a single intravitreal injection of nanoceria into the eyes of VLDLr KO mice at Postnatal day 7 prevents the inherited increase in retinal ROS and ROS-mediated damage by a mechanism involving the inhibition of hypoxia. Our data show that the three major intracellular sources of ROS which are elevated by hypoxia, (NADPH oxidase, mitochondrial oxidative respiration and nitrous oxide synthetase) have decreased production of ROS in the presence of the nanoceria. Secondly, our data show that the nanoceria, by decreasing ROS, also decrease the downstream effects of ROS including: preventing the rise in concentration of retinal VEGF, the development of illicit angiogenesis within the retinal vasculature and the development of choroidal neovascularization (CNV). The third major point is that when the nanoceria are injected at postnatal day 28, all of the disease characteristics which are present at P28 significantly regress (~80%) within one week. This fact provides us with an assay of relatively short duration (1 week) which enables the effectiveness of nanoceria preparations to be evaluated within one week. Fourth, and most important, regarding the present invention, these data demonstrate that VEGF and illicit vessels, present prior to administration of nanoceria decrease and regress when nanoceria are injected. This means that the illicit vessels require ROS. The normal vessels are not affected. This latter point is extremely important with respect to the therapeutic treatment of patients with RAP, AMD, diabetic retinopathy or any other ROS dependent disease because illicit blood vessels in their eyes preferably regress after treatment with the nanoceria without any negative effects on the normal vasculature.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, compositions of matter, means, methods and steps described in the specification. As one of ordinary skill in the art will readily appreciate from the disclosure of the present invention, processes, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, compositions of matter, means, methods, or steps.

Each of the references, patents or publications cited herein is expressly incorporated by reference in its entirety.

What is claimed is:

1. A method of inhibiting, reducing and/or reversing neovascularization associated with a pathological ocular condition in a mammalian subject, the method comprising the steps of:

administering a therapeutically effective amount of a pharmaceutical composition to a mammalian subject exhibiting neovascularization associated with a pathological ocular condition, the pharmaceutical composition comprising cerium oxide nanoparticles and a pharmaceutically acceptable carrier; and reducing at least one of (a) at least one vascular anomaly, (b) the number of illicit neovessels, (c) the rate of retinal neovascularization, and (d) the rate of proliferation of neovascular tissue in the eye of the mammalian subject upon administration of the cerium oxide nanoparticles present in the pharmaceutical composition.

2. The method of claim 1, wherein the at least one vascular anomaly, the number of illicit neovessels, the rate of retinal neovascularization, and/or the rate of proliferation of neovascular tissue in the eye of the mammalian subject is substantially reduced to 25% or less of that observed in the absence of administration of the pharmaceutical composition.

3. The method of claim 1, wherein the at least one vascular anomaly, the number of illicit neovessels, the rate of retinal neovascularization, and/or the rate of proliferation of neovascular tissue in the eye of the mammalian subject is substantially reduced to 10% or less of that observed in the absence of administration of the pharmaceutical composition.

4. The method of claim 1, wherein the at least one vascular anomaly is selected from the group consisting of retinal neovascular lesions, choroidal neovascular lesions, choroidal neovascular tufts, retinal neovascular blebs, and combinations thereof.

5. The method of claim 1, wherein the pathological ocular condition having neovascularization associated therewith is at least one of age-related macular degeneration, diabetic retinopathy, retinitis pigmentosa, retinal detachment, inherited retinal degeneration, Stargardt's disease, and occlusive retinopathy.

6. The method of claim 1, wherein the cerium oxide nanoparticles have a size in a range of from about 1 nanometer in diameter to about 10 nanometers in diameter.

7. The method of claim 1, wherein the cerium oxide nanoparticles have a size in a range of from about 1 nanometer in diameter to about 7 nanometers in diameter.

8. The method of claim 1, wherein the cerium oxide nanoparticles are present in the pharmaceutical composition at a concentration in a range of from about 1 nM to about 1.0 mM.

9. The method of claim 1, wherein the cerium oxide nanoparticles are present in the pharmaceutical composition at a concentration in a range of from about 1 nM to about 50 nM.

10. A method of treating a mammalian subject having at least one neovascular lesion in an eye thereof, the method comprising the steps of:

administering a therapeutically effective amount of a pharmaceutical composition to the eye of the mammalian subject, the pharmaceutical composition comprising cerium oxide nanoparticles and a pharmaceutically acceptable carrier, wherein the cerium oxide nanoparticles have a size in a range of from about 1 nanometer in diameter to about 10 nanometers in diameter and are present in the pharmaceutical composition at a concentration in a range of from about 1 nM to about 1.0 mM; and reducing the at least one neovascular lesion in the eye of the mammalian subject to 50% or less of that observed in the absence of administration of the pharmaceutical composition, and wherein the at least one neovascular lesion is at least one of a retinal neovascular lesion and a choroidal neovascular lesion.

* * * * *

UNITED STATES PATENT AND TRADEMARK OFFICE
CERTIFICATE OF CORRECTION

PATENT NO. : 8,703,200 B2  
APPLICATION NO. : 12/429650  
DATED : April 22, 2014  
INVENTOR(S) : James F. McGinnis et al.

It is certified that error appears in the above-identified patent and that said Letters Patent is hereby corrected as shown below:

In the Specification:  
Column 3, Line 58: Delete "retractile," and replace with -- refractile, --

Signed and Sealed this  
First Day of July, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,703,200 B2  
APPLICATION NO. : 12/429650  
DATED : April 22, 2014  
INVENTOR(S) : James F. McGinnis et al.

Page 1 of 1

It is certified that error appears in the above-identified patent and that said Letters Patent is hereby corrected as shown below:

On the Title Page

Under Item (73) Assignee: After "The Board of Regents of the University of Oklahoma, Norman, OK (US)", insert -- The University of Central Florida Research Foundation, Inc., Orlando, FL (US) --

Signed and Sealed this  
Eighth Day of December, 2020

Andrei Iancu  
*Director of the United States Patent and Trademark Office*